(12) United States Patent
Vincent (10) Patent No.: US 9,616,092 B2
(45) Date of Patent: Apr. 11, 2017

(54) COMPOSITIONS AND METHODS FOR TREATING A PATHOGENIC METABOLIC CONDITION OF THE GUT MICROBIOTA AND DERIVED DISEASES

(71) Applicant: International Nutrition Research Company, Luxembourg (LU)

(72) Inventor: Claude Vincent, Bordeaux (FR)

(73) Assignee: INTERNATIONAL NUTRITION RESEARCH COMPANY, Luxembourg (LU)

( * ) Notice: Subject to any disclaimer, the term of this patent is extended or adjusted under 35 U.S.C. 154(b) by 0 days.

(21) Appl. No.: 14/700,462

(22) Filed: Apr. 30, 2015

(65) Prior Publication Data
US 2016/0287636 A1 Oct. 6, 2016

(30) Foreign Application Priority Data
Mar. 31, 2015 (FR) ...................... 15 52740

(51) Int. Cl.
| | |
|---|---|
| *A01N 65/00* | (2009.01) |
| *A61K 35/20* | (2006.01) |
| *A23L 1/305* | (2006.01) |
| *A61K 38/17* | (2006.01) |
| *A61K 31/198* | (2006.01) |
| *A61K 31/202* | (2006.01) |
| *A61K 31/355* | (2006.01) |
| *A61K 31/405* | (2006.01) |
| *A61K 31/4415* | (2006.01) |
| *A61K 31/519* | (2006.01) |
| *A61K 31/59* | (2006.01) |
| *A61K 33/06* | (2006.01) |
| *A61K 33/24* | (2006.01) |
| *A61K 33/30* | (2006.01) |

(52) U.S. Cl.
CPC ............ *A61K 35/20* (2013.01); *A23L 1/3053* (2013.01); *A23L 1/3056* (2013.01); *A61K 31/198* (2013.01); *A61K 31/202* (2013.01); *A61K 31/355* (2013.01); *A61K 31/405* (2013.01); *A61K 31/4415* (2013.01); *A61K 31/519* (2013.01); *A61K 31/59* (2013.01); *A61K 33/06* (2013.01); *A61K 33/24* (2013.01); *A61K 33/30* (2013.01); *A61K 38/17* (2013.01); *A23V 2002/00* (2013.01); *A61K 2300/00* (2013.01)

(58) Field of Classification Search
CPC ...................................................... A61K 36/00
USPC ........................................................ 424/725
See application file for complete search history.

(56) References Cited

PUBLICATIONS

Goodrich el al., "Human Genetics Shape the Gut Microbiome", Cell 159, 789-799, Nov. 6, 2014, 2014 Elsevier Inc.
Morotomi et al., "Description of *Christensenela minuta* gen. nov., sp. nov., isolated from human faeces, which forms a distinct brand in the order Clostridiales, and proposal of Christenserrellaceae fam. nov." International Journal of Systematic and Evolutionary Microbiology (2012), 62, 144-149.
Damms-Machado et al., "Effects of surgical and dietary weight loss therapy for obesity on gut microbiota composition and nutrient absorption." Biomed Res Int. 2015;2015:806248. doi: 10.1155/2015/806248. Epub Feb. 1, 2015.

*Primary Examiner* — Michael Meller
(74) *Attorney, Agent, or Firm* — Greer, Burns & Crain, Ltd.

(57) ABSTRACT

The invention relates to the use as a drug or medical nutritional product in humans to treat a pathological dysbiosis and/or to prevent or treat at least one derived metabolic disease chosen from among excess weight with comorbidity, obesity, diabetes, heart and vascular diseases, atherosclerosis, degenerative bone disease, neurodegenerative disease, metabolism-related cancers, autoimmune diseases, steatosis, metabolic steatohepatitis, and chronic inflammatory diseases of the intestine, by increasing the *Christensenella* bacterial genus in the intestine, of a composition comprising a mixture of active ingredients consisting of at least:
a whey hydrolysate with a molecular weight comprised between 200 and 10,000 Daltons,
a whey isolate and/or a concentrate, and
calcium caseinate.

12 Claims, 2 Drawing Sheets

COMPOSITIONS AND METHODS FOR TREATING A PATHOGENIC METABOLIC CONDITION OF THE GUT MICROBIOTA AND DERIVED DISEASES

CROSS-REFERENCE TO RELATED APPLICATION

This application claims the benefit of priority from French application 1552740, filed Mar. 31, 2015, the entire disclosure of which is incorporated herein by reference.

TECHNICAL FIELD OF THE INVENTION

The present invention relates to the use of a composition as a drug or a medical nutritional product for the treatment of a pathogenic medical condition of the gut microbiota caused by a pathological dysbiosis of metabolic origin and/or to prevent and treat diseases derived from that pathogenic condition.

BACKGROUND OF THE INVENTION

The microbiota is a set of microorganisms (bacteria, archaea, viruses and eukaryotes) that are specific to each individual. These microorganisms are located on the skin, in the mouth and mainly in the digestive system, which, for $10^{12}$ cells per gram and since there are 1.5 to 2 kg of microbiota, counts the presence of millions of different species, i.e., between 3.3 and 8 million according to the experts, and billions for all microorganisms. This microbiota contains more than one hundred fifty times the genes of the host genome.

The microorganisms of the gut microbiota are classified by kingdom (for example, bacteria), phylum (for example, Firmicutes), class (for example, Clostridia), order (for example, Clostridiales), family (for example, Christensenellaceae), genus (for example, *Christensenella*) and species (for example, *Christensenella minuta*).

Each individual has his own microbiota, which comes from his history and roots. However, in a cohort, 75% of species are found in 50% of the cohort and 57% in 90% of the cohort. More than 85% of species are shared between Europe, the USA and Japan.

The gut microbiota is not homogenous. For a same individual, it varies in quantity and quality from the stomach ($10^1$ with *lactobacillus, vellonella, helicobacter*) to the duodenum, jejunum, ileum ($10^3$ to $10^7$ with *bacilli, streptococcaceae, actinobacteria, actinomycinaeae, corynebacteriaeae*) and lastly the colon ($10^{12}$ with *lachnospiraceae, bacteriodetes*). Certain bacteria (*clostridium, lactobacillus, enterococcus*) are also found in the mucus that coats the gut wall. The major phyla are relatively stable in an individual, and the differences are found in terms of the species, often by several percentage points of the total microbiota. Thus, pathogenic conditions are difficult to detect, since they come from these specific species. The anomalies of the host (genetic and environmental) lie in an imbalanced pathogenic flora called pathogenic dysbiosis; the imbalance threshold is difficult to determine, as are the variations in genuses and species, unless there is a biomarker for the anomaly or the disease. For several years, it has been known that the gut microbiota is not only involved in the digestion and transformation of food into energy, but that it also plays a major role in maintaining good health and in the appearance of several diseases. Recent research suggests that the behavior of the brain, the enteroendocrine system or neurovegetative system, or degenerations, are controlled by the microbiota. It is also known that the gut microbiota is a major regulator in immunity and participates heavily in regulating gene expression of the host.

Through dysbiosis, i.e., a change in the composition of the microbiota, the microbiota may be associated with direct pathogenic metabolic disorders such as type 2 diabetes or cardiovascular disease. Furthermore, certain components of the microbiota have been associated with other diseases such as degenerative diseases, gut diseases and certain types of cancer.

The gut microbiota is also directly correlated with the host's weight. Excess weight with comorbidity and obesity, which are defined by a body mass index (BMI) from 25 to 29.9 for overweight and over 30 for obesity, are in fact associated with a pathological dysbiosis of metabolic origin of the gut microbiota.

Excess weight with comorbidities, obesity and metabolic diseases broadly speaking, are devastating our modern societies, in highly developed countries, emerging countries or even developing countries.

The search for reasons for this epidemic has become critical so as not to see a drop in life expectancy in the next 25 years, and particularly to avoid increasing the number of people in poor health and who are dependent in the end-of-life phase.

The key causes for weight gain are imbalanced food intake, in particular saturated fats, fructose and carbohydrates, which may or may not be associated with a highly sedentary lifestyle relative to food intake, i.e., relative to the quantity of energy. However, not everyone responds in the same way to the same food intake. There are in fact in particular differences in terms of the absorption and storage of energy in the form of fats, and these differences are related to the pathological condition of the gut microbiota.

In case of excess weight and obesity, it has been observed that:
 the richness and diversity of the microbiota decreases
 certain families, genuses and species of pathogens take precedence over others
 the pathogenic microbiota has the ability to extract more energy from foods and non-digestible fibers.

Furthermore, in overweight and obese individuals, a calorie restriction with rebalancing of the diet increases the total richness of the flora by losing body fat mass, but there is a difference in results of the diet depending on the richness of the initial flora. For microbiota that are initially depleted, the results are lower, in particular on the decrease of inflammation and insulin resistance.

Furthermore, the analysis of the microbiota of thin or even anorexic people compared to the obese has established a correlation with certain microorganisms.

A correlation between the phyla and excess weight/obesity has been searched for, and a relationship has been found between the 2 biggest phyla: the relative ratio of Firmicutes to Bacteriodetes increases with the BMI, and the effect on weight loss results in a decrease in the ratio (Damms-machado a 2015, Pekkala s 2015, Remely m 2015, eslinger aj 2014, Bervoets I 2013, Fava f 2013), though this observation has also been invalidated by results demonstrating the opposite (Rahat-Rozenbloom, 2014 Xu P2012, Sefcíková Z 2010).

It is known that the composition of an individual's microbiota is relatively homogenous over time in terms of the phyla (aside from temporary incidents such as antibiotic treatment) but that the genuses may vary, and it is also known that among several individuals, the phyla vary depending on the age, geographical location, ethnicity, lifestyle, etc. It is therefore impossible to establish a standard microbiota for good health, but it is possible to look for the genuses and species that indicate a condition with or without pathology.

Certain enterotypes with the assembly of positive or negative relationships have been determined. In particular, three enterotypes are predominant throughout the world depending on the primacy of the most significant phylum—bacteriodetes, provotella and ruminococcus—but no direct correlation has been able to be established between these enterotypes and metabolic diseases.

For the composition of the microbiota until 2012, it was accepted that the microbiota was built through outside influence and that it was completely acquired from 0 to 3 years through the environment and diet. In a study from November 2014, an international team run by Bruce Ley (Cornell University, NY) published, under the oversight of Julia Goodrich, an article ("*Human genetic shape the gut microbiome*", Cell November 6, 159 789-799), which invalidates the single concept of acquisition by introducing the notion of inheritability for several families, genuses and species; she made this observation by studying a British cohort of monozygotic and dizygotic twins and control persons. The strains of the gut microbiota demonstrated as being inheritable are:

families of bacteria in the Firmicutes:lachanospiraceae, ruminococcaceae and christensenellaceae, an archea in the *Methanogens: M. Smithii*.

The family of the Christensenellaceae is the most transmissible family. It in particular comprises the *Christensenella* genus, and in particular the *Christensanella minuta* species, which has been defined and cultivated recently by Masami Morotomi in Tokyo, described in the study "*Description of christensenella minuta gen. nov.sp.nov. isolated from human faeces, which forms a distinct branch in the other clostridiales, and proposal of christensenellaceae*" (M Morotomi 2012 inter. Jour. of systematic and evolution microbiology 62 144-149).

In children, at birth, the richness of Christensenellaceae is 20% in the meconium versus 8.6% for the mother. This proportion next decreases relatively (to be approximately 5%) through the rapid increase of the other phyla, in particular those that will become preponderant, such as Firmicutes, Bacteriodetes, Proteobacteria and Actinobacteria with the introduction of food (for example, animal fat or proteins) and the environment.

The presence of *Christensenella* is associated with a low BMI as well as a "good health" condition. The higher the relative quantity of *Christensenella* is, the more the host tends to be lean and healthy. Due to its low relative presence, *Christensenella* would become the biomarker for pathogenic dysbiosis, a metabolic pathological condition in particular leading to excess weight with comorbidity, obesity and metabolic diseases.

The family of christensenellaceae is the leader of a "consortium" made up of the following families, ranked by decreasing order of importance in metabolic action: *dehalobacteriaceae* (firmicutes), unclassified *clostridiales, tenericutes* unclassified geniuses ML615J-28 and RF39, *methanobacteriaceae* (euryarchaeota), firmicutes unclassified genus SHA-98, *peptococcaceae, verrucomicrobiaceae*.

The Christensenellaceae family is often positively linked to the abundance of Methagenes, which in turn is correlated to the production of butyrate and propionate, but Christensenellacea does not need this link to express itself in the metabolism, since it contributes directly to the phenotype of the host with which it is associated.

Julia Goodrich ("*Human genetic shape the gut microbiome*" Cell November 6, 159 789-799) continued her observation in germ-free mice seeded with obese microbiota in 2 groups, only one of which received an implantation of *Christensenella*, and that presence caused weight gain of less than 30%.

The Christensenellaceae genus is therefore recognized as a marker of leanness, when it is present in sufficient quantities in the gut microbiota. Furthermore, it is a marker of excess weight and obesity when it is present in small quantities in the gut microbiota. The relative increase of Christensenellacea guarantees weight loss, in particular on the fat mass, and is a driving force for metabolic improvement.

Furthermore, these Christensenellacea bacteria would be involved in other metabolic diseases such as diabetes, heart and vascular disease, atherosclerosis, degenerative bone diseases, neurodegenerative diseases, cancers related to the metabolism, autoimmune diseases and metabolic steatosis and steatohepatitis.

Currently, there is a need for a product capable of acting on the gut microbiota to be able to be used to treat the pathogenic microbiota, and consequently to prevent and treat derived metabolic diseases, such as excess weight with comorbidity, obesity, etc.

SUMMARY OF THE INVENTION

To meet this need, the present invention proposes to use a composition capable of increasing the relative quantity of Christensenellacea in the gut microbiota.

To that end, the invention relates to the use of a composition comprising a mixture of active ingredients made up of at least:

a whey hydrolysate with a molecular weight comprised between 200 and 10,000 Daltons, a whey isolate and/or a concentrate, and calcium caseinate, to be used as a drug or medical nutritional product in humans to treat a pathological condition of the microbiota, namely a metabolic pathological dysbiosis characterized by a drop in Christensenellacea in the gut microbiota. The composition may also be used for the prevention or treatment of at least one derived metabolic disease, in particular a metabolic disease marked by a deficiency of Christensenellacea in the gut microbiota, in particular a metabolic disease marked by a deficiency of Christensenellacea in the gut microbiota chosen from among excess weight with comorbidity, obesity, diabetes, heart and vascular diseases, atherosclerosis, degenerative bone diseases, neurodegenerative diseases, metabolism-related cancers, autoimmune diseases, steatosis, metabolic steatohepatitis and chronic inflammatory diseases of the intestine. The composition treats the pathological microbiota in particular by causing a relative increase in the intestine of the *Christensenella* bacterial genus (phylum Firmicutes, class Clostridia, order Clostridiales, family Christensenellaceae, genus *Christensenella*).

Advantageously, such a composition is able to bring about a relative increase in the quantity of *Christensenella* in the gut microbiota so as to combat metabolic pathogenesis. It may also be used as a drug or medical nutritional product to rebalance the gut microbiota by increasing the *Chris-*

*tensenella* genus and to prevent and combat diseases resulting from that pathological imbalance of the gut microbiota.

DETAILED DESCRIPTION

The invention relates to a composition comprising a mixture of active ingredients made up of at least:
- a whey hydrolysate with a molecular weight comprised between 200 and 10,000 Daltons,
- a whey isolate and/or a concentrate, and
- calcium caseinate, to be used as a drug or medical nutritional product in humans to treat a pathological dysbiosis characterized by a deficiency of *Christensenella* in the gut microbiota and/or to prevent or treat at least one metabolic disease derived from that pathological condition of the gut microbiota chosen from among excess weight with comorbidity, obesity, diabetes, heart and vascular diseases, atherosclerosis, degenerative bone disease, neurodegenerative disease, metabolism-related cancers, autoimmune diseases, steatosis, metabolic steatohepatitis, and chronic inflammatory diseases of the intestine.

The composition acts through a relative increase in the intestine of the *Christensenella* bacterial genus.

The composition is known, but surprisingly and unexpectedly, it acts on the microbiota, and in particular is capable of increasing *Christensenella*.

Within the meaning of the invention, "deficiency" of *Christensenella* in the gut micrograft refers to a level of *Christensenella* in the gut micrograft representing less than 0.01% of the total bacterial genuses detected in the microbiota of a given individual (collected in the stool, the abundance being measured preferably using a Fish sequencing test, or qPCR or meta-analysis).

"*Christensenella*" refers to bacteria in phylum Firmicutes, class Clostridia, order Clostridiales, family Christensenellaceae, and genus *Christensenella*.

Within the meaning of the invention, "medical nutritional composition" or "medical nutritional product" or "medical food" or medical food for special medical purposes or dietary food for special medical purposes refers to a food for therapeutic prevention or treatment use, used alone or in combination with other therapies. It involves a nutritional compound, responding to a particular clinical situation, able to constitute all or part of the food for the patients for whom it is intended.

Within the meaning of the invention, "whey concentrate" refers to a whey extract obtained by concentrating a whey.

Within the meaning of the invention, "pathological dysbiosis" refers to a pathological condition characterized by an imbalance in the distribution of the bacteria of the gut microbiota in terms of the phyla, classes, orders, families, genuses or species, leading to a risk of other metabolic diseases.

Within the meaning of the invention, "whey hydrolysate" refers to any molecule or mixture of molecules obtained using the method comprising a chemical hydrolysis or enzyme hydrolysis step for the whey.

Within the meaning of the invention, "whey isolate" refers to a whey extract that contains less than 1% lactose and fats.

Within the meaning of the invention, "drug" refers to a product having obtained a marketing authorization as a treatment product for a disease.

Within the meaning of the invention, "microbiota" refers to the gut microbiota.

The whey hydrolysate of the composition according to the invention has a molecular weight comprised between 200 and 10,000 Daltons, preferably between 200 and 3,500 Daltons. It is essentially made up of di- and tri-peptides.

Preferably, it is a peptide whey hydrolysate comprising at least 90% peptides by dry weight of the hydrolysate.

The whey isolate and/or concentrate preferably has a molecular weight comprised between 15,000 and 20,000 Daltons.

The whey isolate is preferably manufactured from fresh milk and cheese dairies that do not pasteurize the milk to avoid the destruction of the beta-lactoglobulin and alpha-lactalbumin, and which extract the whey by ultrafiltration or microfiltration (filter size of 0.1 µm). The isolate obtained by ion exchange is less suitable due to its low beta-lactoglobulin and alpha-lactalbumin content level. The isolate contains less than 1% lactose and fats, and its peptide concentration is preferably at least 90% by dry weight.

The whey concentrate is preferably obtained from a cheese dairy whey without pasteurization, containing beta-lactoglobulin, alpha-lactalbumin and glycomacropeptides. The peptide concentration of the concentrate is preferably at least 80% by dry weight.

Furthermore, the calcium caseinate used in the composition according to the invention preferably has a molecular weight comprised between 20,000 and 35,000 Daltons.

Preferably, the weight ratio between the calcium caseinate and the mixture formed by the hydrolysate and the whey isolate and/or concentrate is from 0.8 to 1.2 in the composition. According to one particularly suitable embodiment, the mixture of active ingredients of the composition also comprises a mixture of amino acids.

The amino acids present in composition are preferably at least tryptophan, glutamine, leucine, arginine and/or taurine, but the composition may contain other amino acids, such as isoleucine, valine, phenylalanine or threonine. Very preferably, the composition according to the invention comprises at least tryptophan, leucine, arginine and taurine.

When tryptophan is present, it must make up between 6 and 9%, preferably approximately 7%, by weight of the neutral amino acids present in the composition (leucine, isoleucine, valine, phenylalanine, tyrosine and tryptophan).

When arginine and taurine are present, the weight ratio of arginine to taurine is comprised between 1.5 and 2.

In addition to the mixture of hydrolysate, whey isolate and/or concentrate and calcium caseinate, and amino acids, the mixture of active ingredients of the composition according to the invention may comprise one or more elements chosen from milk calcium, magnesium, vitamin B6, vitamin B9, vitamin E, vitamin D, zinc and chromium.

Likewise, the composition may contain essential fatty acids, in particular omega-3s. Preferably, these are omega-3s of plant origin, with a high proportion of EPA.

According to one preferred embodiment, the mixture of active ingredients of the composition according to the invention comprises at least
- 8 to 12% whey hydrolysate,
- 15 to 20% whey isolate and/or concentrate,
- 20 to 25% calcium caseinate, the percentages being given by dry weight of all of the active ingredients present in the composition (excluding any excipients).

The composition may also contain freely added elements, such as amino acids, vitamins and minerals, which are added to the native components of the whey hydrolysate, the whey isolate, the whey concentrate and the calcium caseinate.

The composition according to the invention is preferably made up of at least:
1.5 to 3% tryptophan,
12 to 20% branched amino acids,
6 to 10% aromatic amino acids,
0.8 to 1.5% taurine,
1.6 to 3% arginine,
1.2 to 3% milk calcium,
0.5 to 1% magnesium,
0.4 to 1% omega-3s,
1 to 2 mg of vitamin B6 per 50 g of composition without excipients,
5 to 15 mg of zinc per 50 g of composition without excipients,
1 to 3 µg of vitamin D per 50 g of composition without excipients,
75 to 150 µg of chromium per 50 g of composition without excipients,
100 µg of vitamin B9 per 50 g of composition without excipients,
10 mg of vitamin E per 50 g of composition without excipients,
the percentages being given by dry weight of all of the active ingredients present in the composition (excluding excipients), part of the components coming from the whey hydrolysate, the whey isolate, the whey concentrate and the calcium caseinate, and the rest being added freely in the form of amino acids, vitamins and minerals.

The branched amino acids of the composition are made up of leucine, isoleucine and valine, preferably:
50 to 60% leucine,
18 to 25% isoleucine, and
20 to 28% valine,
and the aromatic amino acids of tryptophan, phenylalanine and tyrosine, preferably:
15 to 24% tryptophan,
38 to 46% phenylalanine, and
35 to 43% tyrosine.

The composition according to the invention may be obtained using a method as described below:
a first mixture is obtained by mixing components in the following order: calcium caseinate, whey isolate, whey concentrate, whey hydrolysate, free amino acids, magnesium and milk calcium. The pH must be around 7 and stabilized at that level.
adding vitamins, minerals and fatty acids to the initial mixture.

A powder is thus obtained that can be turned into a tablet or liquid, or used in its powdered form in pouches, sticks, cans or gel caps, for example.

When the composition according to the invention is administered orally in a sufficient quantity, it makes it possible to modify the composition of the gut microbiota by causing a relative increase in the quantity of *Christensenella* in the microbiota. The composition makes it possible to reestablish the metabolic functionality through a relative increase of *Christensenella* within the general population of the microbiota, or at least a level making up 0.01% of the total of the bacterial genuses detected in the microbiota of a given individual (collected in the stool, abundance preferably being measured using a Fish sequencing test, or qPCR or meta-analysis).

This increase makes it possible to combat metabolic pathological dysbiosis caused by a deficiency of *Christensenella* in the gut microbiota.

The increased relative quantity of *Christensenella* also makes it possible to prevent or combat metabolic diseases originating from a metabolic pathological dysbiosis characterized by a relative deficiency of *Christensenella* in the gut microbiota, and in particular:
excess weight with comorbidity
obesity
diabetes (and pre-diabetes)
heart and vascular diseases
atherosclerosis
degenerative bone diseases
neurodegenerative diseases, in particular Parkinson's disease and Alzheimer's disease
cancers related to metabolism, in particular esophageal, colon, endometrial, kidney and breast cancer for postmenopausal women,
autoimmune diseases,
steatosis, metabolic steatohepatitis and NASH (nonalcoholic steatohepatitis),
chronic inflammatory diseases of the intestine.

The composition according to the invention is particularly useful for people with a relative proportion of *Christensenella* below 0.01% of all bacterial genuses detected in the microbiota (collected in the stool, abundance preferably being measured using a Fish sequencing test, or qPCR or meta-analysis), and for people with a relative proportion of *Christensenella minuta* in the microbiota below 0.005% of the total abundance of the gut flora, i.e., the total bacterial species detected in the microbiota (collected in the stool, abundance preferably being measured by a Fish sequencing test, or qPCR or meta-analysis). Different methods may be used to analyze the microbiota (the collection generally being done in the stool):
culture using traditional bacterial culture methods known by those skilled in the art
biological methods through the 16SrRNA marker
sequencing either using the SANGER method with Operational Taxonomic Units, or by pyrosequencing at the 16SrRNA (method used in studying the composition)
imprint by electrophoresis, polymorphism and ribosomal, DNA with micro areas,
FISH (fluorescence in situ hybridization) and qPCR (quantitative polymerase chain reaction) with amplification of a group,
meta-analysis with meta-genomics (composition and function of all of the genes), metaproteomics (protein analysis), metabolomics (metabolic profiling) and metatranscriptomics (through the RNA).

According to one alternative, in case of an extreme medical emergency, it is possible, for people with a *Christensenella* deficiency, to implant bacteria of the *Christensenella* genus in the intestine prior to the administration of the composition according to the invention, by using a specific probiotic for that type of bacteria in a capsule or by direct implantation by lead in the jejunum. The implantation should represented 75 to 100 mg of *Christensenella* bacteria. The implanted bacteria may be bacteria obtained by culturing bacteria from the genus *Christensenella* taken from the stool of the treated person if there are traces or from bacteria obtained by culturing bacteria from the genus *Christensenella* taken from the stool of lean and healthy people.

The use of the composition according to the invention in appropriate quantities makes it possible, optionally with prior implantation, to bring the presence of *Christensenella* to a minimum relative proportion of 0.01% relative to all of the taxa of the microbiota collected in the stool. The composition may also make it possible to obtain a relative quantity of *Christensenella minuta* (when the analysis method makes it possible to go down to the species level) of at least 0.0075% (relative to all of the taxa of the microbiota collected in the stool).

Surprisingly, the composition according to the invention is also capable of regulating, in the microbiota, the families of bacteria known for their relatively significant presence in excess weight, obesity and metabolic diseases, chosen from among clostridiales, in particular Lachnospiraceae and clostridiaceae.

Also astonishingly, it is also able to regulate, in the microbiota, the families of bacteria known for their ability to increase the quantity of energy taken from food, chosen from among bacteria which yield butyrate and propionate by fermentation, but also increase energy through the digestion of fibers that are not normally digested, namely: *Roseburia*, *Faecalbacterium* (in particular the species *prausnitzii*), *Akkermansia* (in particular the species *municiphali*), *Eubacterium* (in particular the species *rectale*), *Methanobrevibacter* (in particular the species *smithii*). This additional energy transformation is one of the likeliest causes of the excess weight epidemic and metabolic dysfunction. It is necessary to decrease these "energizers", but without creating a deficiency, since the microbiota is a major consumer of butyrate, propionate and acetate (in order of importance); the genus *Akkermansia* and species *Akkermansia municiphali* (also inheritable) are particularly important, since they are the main producers of propionate, which guarantees proper operation of the gut barrier by limiting the passage of LPS; in fact, the latter, induced by diets too high in fat (saturated in particular), is the first to blame for metabolic dysfunction, steatosis, hepatitis and the formation of adipose tissue. The regulation by the invention of 2 inheritable genes *christensenella* and *akkermansia* that are difficult to alter is essential to restore the proper operation of the metabolism and also serve as markers for success of the intervention using treatment according to the invention.

The composition according to the invention may assume any suitable form for oral administration. It may in particular assume the form of a powder or granules, ready-to-use beverages, bars or extruded products, capsules, gel caps, dispersible tablets or any other suitable pharmaceutical form, the composition being supplemented with excipients and traditional fillers known by those skilled in the art.

The daily dose of composition according to the invention (dose of mixture of active ingredients without the excipients) is preferably comprised between 66 and 110 g, preferably in two administrations of 33 to 55 g distributed one in the morning as breakfast or at 11 AM as a snack, and the other as an afternoon snack.

Advantageously, with the goal of weight loss, the bioavailability in the body of the amino acids, peptides and proteins present in the composition in the body is comprised between 10 minutes and 5 hours, which allows a rapid action that lasts over time so as to limit the quantity of food to be consumed daily.

Furthermore, the presence of the milk calcium makes it possible to improve the palatability of the dietary product according to the invention, in particular by hiding the bitter taste of the whey hydrolysate, such that it contributes to eliminating the risk of people ceasing to consume it for taste reasons and abandoning their treatment before it is complete.

The composition according to the invention falls within customized medicine and is a major advance in particular in pharmaco-metabolic medicine.

The composition according to the invention may in fact be used as a treatment adapted to the metagenomics of the treated individual.

Thus, before treatment using the composition according to the invention, a test may be done to detect the presence or absence of *Christensenella* and its proportion in the microbiota. This test makes it possible to establish a likelihood of total or partial success or failure of the treatment. The test may be repeated at the end of treatment to analyze the increased level of the bacteria, then at one year to measure the lastingness of the treatment and risk of relapse with the possibility of performing another preventive treatment. The test may also relate to other bacteria, in particular *Akkermansia*. The advantage lies in no longer treating blindly and monitoring the patient's chronic disease for life.

The invention thus makes it possible to resolve the problems of therapeutic failures, of which there are many, either due to abandonment of the treatment in progress, and most often at the beginning, or due to regaining weight after several months or years after significant weight loss. Failures are attributed to the lack of motivation or disinterest in making permanent efforts, but the blockage may be due to the near or complete absence of *Christensenella* in the microbiota.

The invention is now illustrated through a non-limiting example of a dietary composition, assuming the form of a powder of 55 g (active ingredients and excipients) packaged in a pouch.

This composition is obtained from the following active ingredients:
  5 g of whey hydrolysate with a molecular weight between 200 and 3,500 Daltons,
  10 g of whey isolate and/or concentrate with a molecular weight between 15,000 and 20,000 Daltons,
  13 g of calcium caseinate with a molecular weight between 20,000 and 35,000 Daltons,
  1 mg of vitamin B6,
  10 mg of zinc,
  0.45 g of taurine,
  40 µg of chromium,
  10 mg of vitamin E,
  100 µg of vitamin B9,
  2.5 µg of vitamin D,
  270 mg of plant omega-3s,
  q.s. 4.2 g of leucine,
  q.s. 0.8 g of tryptophan,
  q.s. 0.9 g of arginine,
  q.s. 0.75 g of milk calcium,
  q.s. 0.36 g of magnesium.

"q.s. X g" of an element of the competition refers to the total quantity of that element in the composition: quantity provided by the proteins (calcium caseinate, whey isolate, whey concentrate, whey hydrolysate) and completed by the addition of the element in free form to arrive at X g.

The invention is now illustrated through a study showing the effect of the composition in the gut microbiota, in particular on *Christensenella*.

The study pertained to 54 subjects. This is an ancillary study to a random, blind international clinical study with another active product as control. Two ancillary studies were conducted on 54 subjects, one on the microbiota and the other on the adipose tissue.

The clinical study pertained to 108 patients whose characteristic was being overweight or obese with at least 3 proven comorbidity factors; the subjects were enrolled during a visit comprising the morphological criteria, a CT scan, a DEXA, and a complete biological analysis. For the ancillary study on 54 subjects, a sample of subcutaneous adipose tissue and stool samples were also taken. The subjects received either the composition according to the invention or an isocaloric active control corresponding to the composition according to the invention, but in which the whey was replaced by a pea protein, known for its action on the microbiota.

The study of the microbiota included a withdrawal upon enrollment and another during the visit in week 12, at the end of treatment with the product with moderate calorie restriction. The stool was frozen, and at the end of the study, it was analyzed by pyrosequencing. The analyses were conducted by the primary investigator, the Institut du Cardiométabolisme et Nutrition de Paris.

Out of the 54 subjects, 27 were treated with the composition according to the invention (composition of the example) and 27 with the control product.

Stools were collected upon enrollment and at the end of treatment in week 12 with the 2 products and a calorie restriction of 600 kcal.

Figure 1:
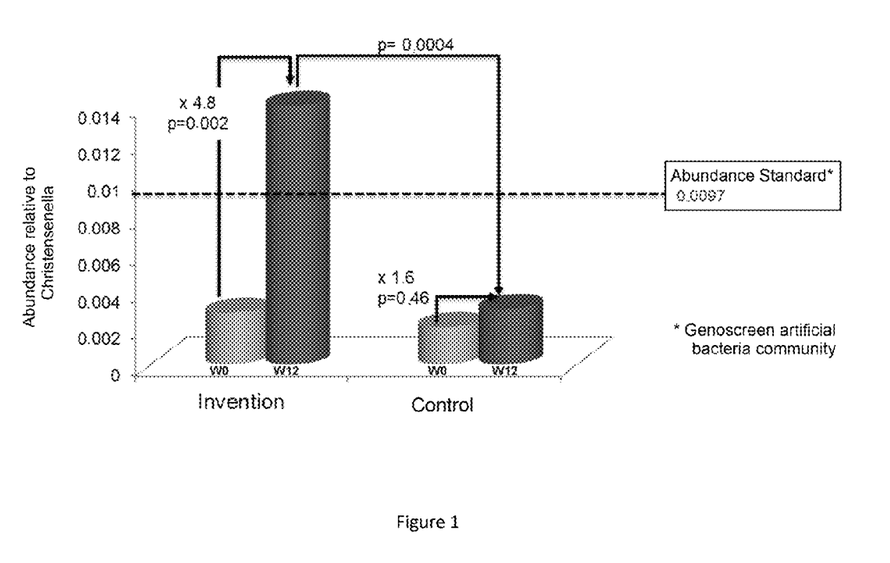
FIG. 1: a diagram of the results of table 1 relative to the relative abundance of *Christensenella*.

The results for the study of the microbiota are shown in table 1 below, and in FIGS. 1 and 2.

Figure 2:
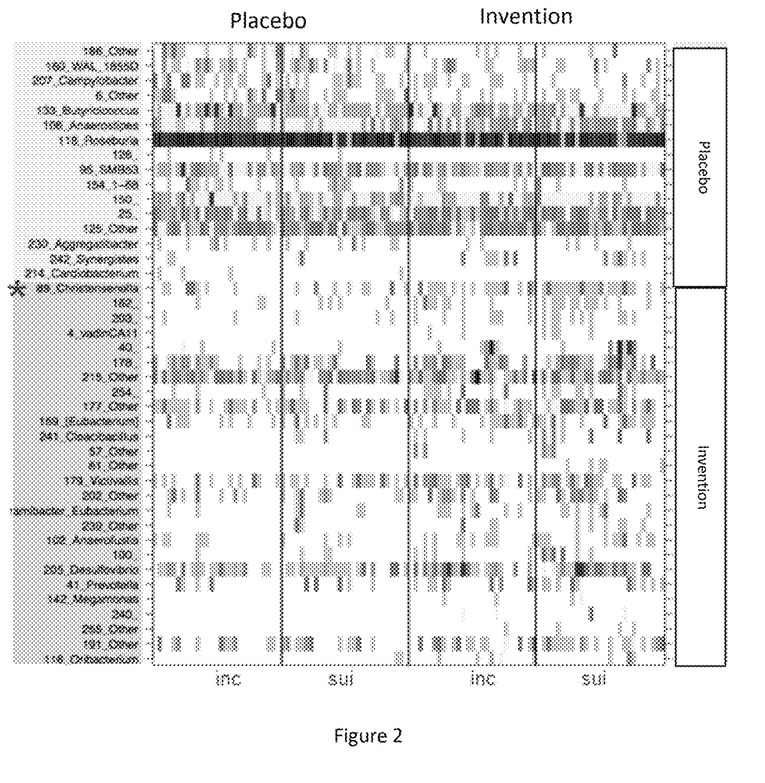
FIG. 2: a barcode table, done by E. Prifti, of the results obtained in the study done on the gut microbiota of patients treated with a placebo and patients treated according to the invention.

For the results shown in FIG. 2, the following items should be noted. the Wilcoxon test between genuses was done based on a normalized abundance, at value $p<0.05$, 16 genuses are more abundant with placebo treatment and 26 genuses with the treatment according to the invention, only one genus resists multiple tests, i.e., *Christensenella*.

TABLE 1

| | STANDARD Artificial bacteria community (1) | | INVENTION | | | | | CONTROL | | | | |
|---|---|---|---|---|---|---|---|---|---|---|---|---|
| | Relative presence | READS | PR W0 | PR W12 | READS W0 | READS W12 | Δ% | PR W0 | PR W12 | READS W0 | READS W12 | Δ% |
| POPULATION | | | | | 27 | | | | | | | |
| TOTAL TAXA | 100 | 82394 | 100 | 100 | 75,875 | 74,220 | −1.5 | 100 | 100 | 73,838 | 72,365 | −1.2 |
| FIRMICUTES | 72.9 | 60019 | 67.2 | 68.2 | 51,260 | 50,633 | 12.0 | 69.3 | 63.5 | 51,953 | 45,953 | −7.4 |
| BACTERIODETES | 20.7 | 17057 | 19.9 | 22.4 | 14,863 | 16,660 | 16 | 20.5 | 25.9 | 15,063 | 18,724 | 21.3 |
| PROTEOBACTERIA | 3.0 | 2470 | 7 | 4.8 | 5,430 | 3,538 | −20.6 | 5.8 | 6.8 | 4,281 | 4,962 | 16.5 |
| ACTINOBACTERIA | 5.0 | 4148 | 2.3 | 1.7 | 1,721 | 1,264 | −16.3 | 2.6 | 2.1 | 1,896 | 1,496 | −12.3 |
| FIRMICUTES/ BACTERIODETES | | | 3.5 | N | 3.4 | 3.0 | | | | 3.4 | 2.5 | NS |
| OVERWEIGHT CONSORTIUM (2) | 22 | 18,147 | 22.2 | 19.8 | 17,093 | 14,670 | −9 | 25.3 | 25.0 | 18,730 | 18,110 | 0.5 |
| ENERGIZER CONSORTIUM (3) | 5.2 | 4,290 | 8.7 | 8.2 | 6,592 | 6073 | −6 | 10.5 | 12.0 | 7,801 | 8,670 | 13 |
| of which AKKERMANSIA | NC | NC | 0.0161 | 0.0337 | 12 | 25 | 118 | 0.0097 | 0.0186 | 7 | 13.5 | 57% |
| CHRISTEN-SENELLACEAE CONSORTIUM (4) | 11.5 | 9,494 | 11.4 | 11.4 | 8,389 | 8,486 | 1.6 | 0.07 | 11.0 | 8,982 | 8,630 | −3.8 |
| *CHRISTENSENELLA* GENUS | 0.0097 | 8 | 0.0028 | 0.013 | 2 | 10 | 380 | 0.002 | 0.0027 | 1.5 | 2 | 60% |

(1) there is no ideal microbiota model, since it is individual and depends on the genetics and experience of each person; for the study, a standard of the cultivated families was developed; this standard was used to replace the results in a context
(2) the overweight consortium comprises many families, in particular in the clostridiales order, but 2 appear to be important due to their number and force of impact: lachnospiraceae and clostridiaceae
(3) the consortium of "energizers" are the bacteria which yield butyrate and propionate by fermentation, but also increase energy through the digestion of fibers not normally digested; it is made up of: *Roseburia*, Faecalbacterium, *Akkermansia*, Eubacterium, *Methanobrevibacter*. Balance is particularly important in this group.
(4) the christensenellaceae consortium comprises the families: Christensenellaceae, Methanobacteriaceae, Dehalobacteriaceae, Peptococcaceae, Verrucomicrobiaceae, Clostridiales-nonclassified (in the present study, unclassified clostridiales were included, as well as others to give weight to that family).

Out of the total microbiota, a relative depletion should be noted for both the Invention and Control groups relative to the standard, which is explained by the metabolic situation of those 2 groups; treatment does not improve this general situation, which is logical, since 12 weeks is an insufficient length of time for the major phyla.

Out of the mass of traditional major firmicute and bacteriodete phyla and their relationship, there is a relative depletion, but above all for the firmicutes, which can be explained by the insulin resistance and very advanced inflammation situation; the situation improves slightly on average for groups treated with the composition according to the invention. In terms of the relationship (currently controversial), the situation is improving, but more for the control group also through a deterioration of the firmicutes, which shows that this ratio is not particularly interesting.

In the other 2 major phyla, the Proteobacteria are high and the Actinobacteria are low; these results perfectly reflect the metabolic situation of these subjects; there is a favorable relative evolution for the group according to the invention in both phyla.

The overweight consortium evolved favorably for the invention, but in the opposite direction for the control.

The energizer consortium, which is high in both groups, is being resized for the group according to the invention, unlike the control group; *Akkermansia*, which was particularly low, is resized in both groups, but with a more significant increase for the group according to the invention.

The Christensenellaceae consortium (Goodrich 2013) increases in the groups treated according to the invention, reflecting the improvement in terms of the metabolic level and weight loss.

In the study of the Christensenellaceae family, the unclassified genuses not belonging to Christensenellacea are crucial (>99%). According to a 2013 publication by Rajilic-Strojanovic, these unclassified genuses are involved in the inflammation of inflammatory bowel disease. Here there is a relative decrease for treatment according to the invention from 1.26 to 1.12 and an increase for the control from 0.83 to 0.89. However, since several genuses should exist in this unclassified part and that could evolve in divergent ways, it is impossible to draw conclusions from this; it is advisable to wait for new discoveries in these unclassified genuses.

The analysis of the *christensenella* genus is at the core of this study on microbiota. Christensenellaceae is an "inheritable" bacteria and is not acquired and not sensitive to diet; in this category, it seems to be the most important in the group. This implies that for people with a low Christensenellaceae level, it is "vital" to reestablish a healthy metabolism, to increase this genus rather than all of the microbiota with prebiotics or probiotics, which can cause increases in undesirable classes, such as methanogens or helicobacters. The invention has a targeted action on the bacteria, useful for the metabolism. The regulation of *Akkermansia* is second in terms of priority, then those of the consortium on weight and energizers.

Furthermore, Christensenellaceae is a marker bacteria for "normal" weight from the metabolic perspective, and a good health marker, therefore a microbiota that works regularly without pathogenicity both genetically and in terms of lifestyle. Furthermore, Goodrich has demonstrated that the implantation of Christensenellaceae reversed the weight curve through a lower weight gain in mice, which is reflected in humans by weight loss.

The action of Christensenellaceae is particularly essential for metabolic regulation in order to erase the pathogenic factors that result in metabolic diseases.

The Christensenellaceae genus is relatively underrepresented in both groups (0.0028 and 0.002 versus 0.0097) relative to the standard, which confirms the decrease of this genus in a population suffering from metabolic issues. The action of the 2 products causes Christensenellaceae to increase from 0.0028% to 0.014% for the group according to the invention (380%), with a significance relative to the initial level (p=0.002), while the control goes from 0.002% to 0.0028% (+60% and not significant). In 12 weeks, the group treated according to the invention very clearly goes above the standard (0.014% versus 0.0097%), and it is significant relative to the control (0.004).

Furthermore, it should be noted that of all of the genuses comprised in the human microbiota (1,500 known at this time), the only significant genus in the study on the invention that emerges from all of the statistical tests is Christensenellaceae, which appears to be one of the most significant genuses for metabolic pathological conditions of the microbiota and derived metabolic diseases.

Furthermore, the clinical results and the ancillary study on the adipose tissue are shown in table 2 below:

TABLE 2

| | Composition according to the invention | |
|---|---|---|
| | TOTAL FAS Base Line | TOTAL FAS Δ% AT 12 WEEKS |
| CLINICAL STUDY | | |
| POPULATION | 108 | |
| VISCERAL BODY FAT MASS CT Scan cm² | 192.3 | −10.4% |
| TOTAL BODY FAT MASS CT Scan cm² | 489.7 | −8.9% |
| BODY FAT MASS DXA kg | 37.0 | −8.9% |
| LEAN BODY MASS DXA kg | 51.2 | −0.1% |
| WAIST SIZE cm | 104.5 | −4.2% |
| WEIGHT kg | 92 | −3.9% |
| TAS mm | 131.7 | −2.7% |
| TAD mm | 81.6 | −4.0% |
| GLYCEMIA mmol | 5.5 | −2.8% |
| INSULINEMIA mUI/l | 12.6 | −19.0% |
| HOMA IR | 3.1 | −20.5% |
| HOMA B | 124 | −9.3% |
| HOMA S | 59.9 | +40.6% |
| TOTAL CHOLESTEROL mmol | 5.2 | −7.2% |
| HDL mmol | 1.2 | +0.2% |
| LDL mmol | 3.2 | −7.6% |
| TRIGLYCERIDES mmol | 1.6 | −9.6% |
| TNF pg/ml | 1.9 | −10.2% |
| ANCILLARY STUDY ADIPOSE TISSUE | | |
| GLYCEROL pg/ml | 16 | −20.1% |
| IL6 | 3707 | −13.3% |
| O² ENERGY CONSUMPTION μM | 0.002 | +63% |
| ADIPONECTIN pg/ml | 11426 | +13.3% |

One can see that the composition used according to the invention has an unquestionable action on the metabolic function of the adipocyte, which results in increased adiponectin in the adipose tissue, which reflects the two basic dysfunctions at the origin of many metabolic and degenerative diseases:
  inflammation with a decrease in IL6 in the adipose tissue and TNFα in the plasma, which is explained by the activation of p105 on the adipocytes, which regulates NFκB, the inflammatory cytokine modulator.
  insulin resistance, which improves with a decrease in the insulinemia, decreased HOMA IR, but above all a very significant improvement in insulin sensitivity by HOMA S.
  two other functions on the adipose tissue should be noted: the regulation of the lipolysis of the adipocytes of people who are overweight (glycerol) and increased energy production (O² consumption)
  improved comorbidity factors: blood pressure, glycemia, insulinemia, cholesterol, LDL and triglycerides, is both a consequence of metabolic improvement and the direct action of the active compounds of the invention, in particular amino acids
  lastly, furthermore, no serious side effects were noted during treatment aside from several temporary digestive difficulties.

According to the invention, it is thus possible to act on a pathological dysbiosis of the gut flora through a relative increase in the *Christensenella* genus, and consequently also to act on the metabolic diseases marked by this pathology. The actions on other families, genuses or species reinforce the action of *Christensenella*.

What is claimed is:

1. A method of treating a human suffering from a disease, the method comprising administering to said human suffering from a disease a composition consisting essentially of therapeutically effective amounts of a mixture of:
   a) whey hydrolysate;
   b) a component selected from the group consisting of whey isolate, whey concentrate, and a combination thereof; and
   c) calcium caseinate to effectively treat the disease in said human suffering therefrom, wherein said disease is selected from the group consisting of heart disease, atherosclerosis, degenerative bone disease, Parkinson's disease, Alzheimer's disease, metabolic steatosis, and steatohepatitis.

2. The method of claim 1, wherein the human's gut microbiota is deficient for *Christensenella*.

3. The method of claim 1, wherein the whey hydrolysate has a molecular weight from 200 to 3,500 Daltons, the whey isolate has a molecular weight in the range from 15,000 to 20,000 Daltons, and the calcium caseinate has a molecular weight in the range from 20,000 to 35,000 Daltons.

4. The method of claim 1, wherein the weight ratio between the calcium caseinate and a mixture formed by mixing the whey hydrolysate and the whey isolate is in a range from 0.8 to 1.2 and wherein the whey hydrolysate is present between 8% and 12%, at least one from the whey isolate and the whey concentrate is present between 15% and 20%, and the calcium caseinate is present between 20 and 25%, the percentages being based on the total dry weight of the whey hydrolysate, whey isolate, and calcium caseinate present in the composition.

5. The method of claim 1, wherein the mixture of whey hydrolysate, at least one from whey isolate and whey concentrate, and calcium caseinate also consists essentially of a mixture of free amino acids selected from the group consisting of tryptophan, glutamine, leucine, arginine and taurine.

6. The method of claim 5, wherein the tryptophan makes up between 6 and 9% by weight of the neutral amino acids present in the composition.

7. The method of claim 5, wherein the weight ratio of arginine to taurine is in the range from 1.5 to 2.

8. The method of claim 5, wherein the mixture of whey hydrolysate, whey isolate, and calcium caseinate also consists essentially of an element selected from the group consisting of milk calcium, magnesium, vitamin B6, vitamin B9, vitamin E, vitamin D, zinc, chromium and omega-3s.

9. The method of claim 1, wherein the composition also consists essentially of at least one of the following:
   1.5 to 3% tryptophan,
   12 to 20% branched amino acids,
   6 to 10% aromatic amino acids,
   0.8 to 1.5% taurine,
   1.6 to 3% arginine,
   1.2 to 3% milk calcium,
   0.5 to 1% magnesium,
   0.4 to 1% omega-3s,
   1 to 2 mg of vitamin B6 per 50 g of composition without excipients,
   5 to 15 mg of zinc per 50 g of composition without excipients,
   1 to 3 µg of vitamin D per 50 g of composition without excipients,
   75 to 150 µg of chromium per 50 g of composition without excipients,
   100 µg of vitamin B9 per 50 g of composition without excipients,
   10 mg of vitamin E per 50 g of composition without excipients,
   the percentages being given by dry weight of all of the active ingredients present in the composition.

10. The method of claim 1, wherein the composition is administered in a form selected from the group consisting of powder, granules, a ready-to-use beverage, food bar, an extruded form, capsules, gel caps, and dispersible tablets.

11. The method of claim 1, wherein the human is afflicted by pathological dysbiosis of the gut microbiota.

12. The method of claim 1, wherein the human is presented with at least one of the following symptoms: excessive weight and metabolic dysbiosis.

* * * * *